US012590044B2

(12) United States Patent
Al Khunaizi et al.

(10) Patent No.: US 12,590,044 B2
(45) Date of Patent: Mar. 31, 2026

(54) METHODS OF PREPARING CRACKING CATALYST WITH ALUMINA BINDER AND PHOSPHORIC ACID

(71) Applicant: Saudi Arabian Oil Company, Dhahran (SA)

(72) Inventors: Hashim N. Al Khunaizi, Qatif (SA); Munir Khokhar, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 538 days.

(21) Appl. No.: 18/334,086

(22) Filed: Jun. 13, 2023

(65) Prior Publication Data

US 2024/0417344 A1     Dec. 19, 2024

(51) Int. Cl.
| | |
|---|---|
| *C07C 4/06* | (2006.01) |
| *B01J 29/40* | (2006.01) |
| *B01J 35/61* | (2024.01) |
| *B01J 37/00* | (2006.01) |
| *B01J 37/02* | (2006.01) |
| *B01J 37/08* | (2006.01) |
| *C07C 11/06* | (2006.01) |

(52) U.S. Cl.
CPC ................ *C07C 4/06* (2013.01); *B01J 29/40* (2013.01); *B01J 35/615* (2024.01); *B01J 37/0009* (2013.01); *B01J 37/0072* (2013.01); *B01J 37/0211* (2013.01); *B01J 37/08* (2013.01); *C07C 11/06* (2013.01); *B01J 2229/16* (2013.01); *B01J 2229/18* (2013.01); *C07C 2529/40* (2013.01)

(58) Field of Classification Search
CPC ...... B01J 29/40; B01J 35/615; B01J 37/0009;
B01J 37/0072; B01J 37/0211; B01J 37/08; B01J 37/28; B01J 2229/16; B01J 2229/18; C07C 4/06; C07C 11/06; C07C 2529/40

See application file for complete search history.

(56) References Cited

U.S. PATENT DOCUMENTS

| | | | |
|---|---|---|---|
| 5,288,739 | A | 2/1994 | Demmel |
| 6,964,935 | B2 | 11/2005 | Harris et al. |

(Continued)

FOREIGN PATENT DOCUMENTS

| | | | | |
|---|---|---|---|---|
| WO | WO-2012085690 A1 | * | 6/2012 | ............... C07C 1/20 |

OTHER PUBLICATIONS

Machine translation of Almanza et al (WO 2012/085690). (Year: 2012).*

(Continued)

*Primary Examiner* — Brian A McCaig

(74) *Attorney, Agent, or Firm* — DINSMORE & SHOHL LLP

(57) ABSTRACT

A method for preparing a cracking catalyst includes combining a zeolite, an alumina binder, and phosphoric acid to form an extrusion mixture. The phosphoric acid acts as a peptizing agent. The extrusion mixture comprises from 0.000271 weight percent to 0.1 weight percent phosphoric acid based on the total weight of the extrusion mixture. The method further includes extruding the extrusion mixture to produce an extrudate. During the extruding, the phosphoric acid peptizes the alumina binder in the extrudate. The method further includes drying and calcining the extrudate to produce the cracking catalyst.

19 Claims, 4 Drawing Sheets

(56)  References Cited

U.S. PATENT DOCUMENTS

| | | | |
|---|---|---|---|
| 10,888,852 B2 | 1/2021 | Ludvig et al. | |
| 2014/0007493 A1 | 1/2014 | Henry et al. | |
| 2015/0306575 A1* | 10/2015 | Mandan | B01J 23/883 |
| | | | 502/200 |

OTHER PUBLICATIONS

Lowen et al., "Undestanding the Activation of ZSM-5 by Phosphorus: Locallizing Phosphate Groups in the Pores of Phosphate-Stabilized ZSM-5", Chemistry of Materials, vol. 32, pp. 9390-9403, 2020.

* cited by examiner

METHODS OF PREPARING CRACKING CATALYST WITH ALUMINA BINDER AND PHOSPHORIC ACID

BACKGROUND

Field

The present disclosure relates to methods of preparing catalysts and processes for processing hydrocarbon materials and, in particular, methods of preparing cracking catalysts and processes for cracking butenes to produce propylene and ethylene.

Technical Background

The worldwide increasing demand for light olefins remains a major challenge for many integrated refineries. In particular, the production of some valuable light olefins, such as ethylene and propylene, has attracted increased attention as pure olefin streams are considered the building blocks for polymer synthesis. The production of light olefins depends on several process variables, such as the feed type, operating conditions, and the type of catalyst. Despite the options available for producing a greater yield of propylene and light olefins, intense research activity in this field is still being conducted. For example, light olefins are typically produced through thermal cracking (or steam pyrolysis) of petroleum gases and distillates, such as naphtha, kerosene, or gas oil. Light olefins may also be produced through fluid catalytic cracking processes. However, these processes generally produce a significant amount of lower value component streams, such as C4 streams comprising mixed butenes, and mixed butanes, which have lower value compared to ethylene and propylene.

SUMMARY

Accordingly, there is an ongoing need for cracking catalysts and processes for cracking C4-containing streams to produce greater yields of propylene and ethylene. The present disclosure is directed to methods of preparing cracking catalysts and processes for catalytic cracking of mixed butenes to produce greater yields of propylene and ethylene. The cracking catalyst of the present disclosure comprises a zeolite and an alumina binder. The cracking catalyst further comprises phosphorous. The cracking catalyst further comprises a very low phosphorous content, such as from 0.000271 weight percent to 0.1 weight percent phosphorous. The zeolite has a high silica to alumina molar ratio of greater than or equal to 500. The processes of the present disclosure include contacting a feed stream comprising butenes with the cracking catalyst under reaction conditions sufficient to convert at least a portion of butenes to at least propylene.

According to at least one aspect of the present disclosure, methods of preparing the cracking catalyst of the present disclosure include combining a zeolite, an alumina binder, and phosphoric acid to form an extrusion mixture. The phosphoric acid acts as a peptizing agent. The extrusion mixture comprises from 0.000271 weight percent to 0.1 weight percent phosphoric acid based on the total weight of the extrusion mixture. The extrusion mixture is extruded to produce an extrudate. During extruding, the phosphoric acid peptizes the alumina binder in the extrudate. The extrudate may be dried and calcined to produce cracking catalyst.

Additional features and advantages of the aspects of the present disclosure will be set forth in the detailed description that follows and, in part, will be readily apparent to a person of ordinary skill in the art from the detailed description or recognized by practicing the aspects of the present disclosure.

BRIEF DESCRIPTION OF THE DRAWINGS

The following detailed description of the present disclosure may be better understood when read in conjunction with the following drawings in which.

Figure 1:
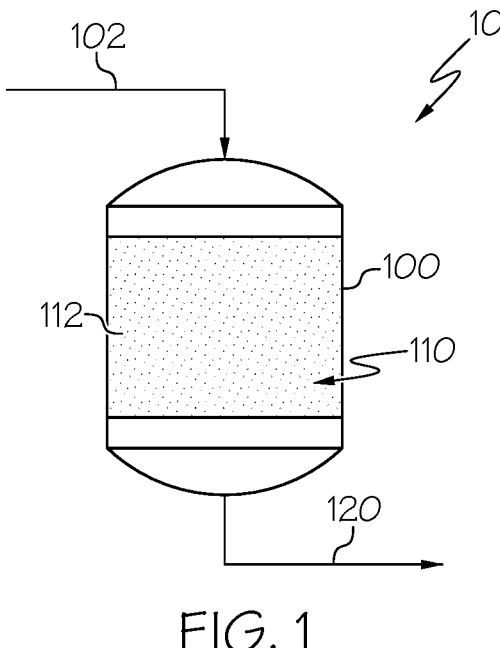
FIG. 1 schematically depicts a generalized flow diagram of a fixed bed reactor system for converting mixed butenes to propylene, ethylene, or both through catalytic cracking, according to one or more embodiments shown and described in the present disclosure.

When describing the simplified schematic illustrations of FIGS. 1-6, the numerous valves, temperature sensors, electronic controllers, and the like, which may be used and are well known to a person of ordinary skill in the art, may not be included. Further, accompanying components that are often included in systems such as those depicted in FIGS. 1-6, such as air supplies, heat exchangers, surge tanks, and the like also may not be included. However, a person of ordinary skill in the art understands that these components are within the scope of the present disclosure.

Additionally, the arrows in the simplified schematic illustrations of FIGS. 1-6 refer to process streams. However, the arrows may equivalently refer to transfer lines, which may transfer process steams between two or more system components. Arrows that connect to one or more system components signify inlets or outlets in the given system components and arrows that connect to only one system component signify a system outlet stream that exits the depicted system or a system inlet stream that enters the depicted system. The arrow direction generally corresponds with the major direction of movement of the process stream or the process stream contained within the physical transfer line signified by the arrow.

The arrows in the simplified schematic illustrations of FIGS. 1-6 may also refer to process steps of transporting a process stream from one system component to another system component. For example, an arrow from a first system component pointing to a second system component may signify "passing" a process stream from the first system component to the second system component, which may comprise the process stream "exiting" or being "removed" from the first system component and "introducing" the process stream to the second system component.

Reference will now be made in greater detail to various aspects, some of which are illustrated in the accompanying drawings.

DETAILED DESCRIPTION

The present disclosure is directed to methods of preparing cracking catalysts and processes for catalytic cracking of butenes to produce at least propylene. The cracking catalyst of the present disclosure may be prepared by combining a zeolite, an alumina binder, and phosphoric acid to form an extrusion mixture. The phosphoric acid may act as a peptizing agent. The extrusion mixture may comprise from 0.000271 weight percent (wt. %) to 0.1 wt. % phosphoric acid based on the total weight of the extrusion mixture. The extrusion mixture may be extruded to produce an extrudate. During the extruding, the phosphoric acid may peptize the alumina binder in the extrudate. The extrudate may be dried and calcined to produce the cracking catalyst. When contacted with a feed comprising butenes, the cracking catalyst may provide increased selectivity toward producing olefins and increased olefin yield by weight of the product.

As used in the present disclosure, the term "cracking" refers to a chemical reaction where a molecule having carbon-carbon bonds is broken into more than one molecule by the breaking of one or more of the carbon-carbon bonds; where a compound including a cyclic moiety, such as an aromatic, is converted to a compound that does not include a cyclic moiety; or where a molecule having carbon-carbon double bonds are reduced to carbon-carbon single bonds. As used in the present disclosure, the term "catalytic cracking" refers to cracking conducted in the presence of a catalyst. Some catalysts may have multiple forms of catalytic activity, and calling a catalyst by one particular function does not render that catalyst incapable of being catalytically active for other functionality.

As used in the present disclosure, the term "catalyst" refers to any substance that increases the rate of a specific chemical reaction, such as but not limited to cracking reactions.

As used in the present disclosure, the term "used catalyst" refers to catalyst that has been contacted with reactants at reaction conditions, but has not been regenerated through a regeneration process. The "used catalyst" may have coke deposited on the catalyst and may include partially coked catalyst as well as fully coked catalysts. The amount of coke deposited on the "used catalyst" may be greater than the amount of coke remaining on the regenerated catalyst following regeneration.

As used in the present disclosure, the term "regenerated catalyst" refers to catalyst that has been contacted with reactants at reaction conditions and then regenerated through a regeneration process to restore at least a portion of the catalytic activity of the catalyst. The "regenerated catalyst"

may have less coke compared to used catalyst and may have greater catalytic activity compared to used catalyst. In some instances, "regenerated catalyst" may have more coke and lesser catalytic activity compared to fresh catalyst that has not been contacted with reactants a cracking reaction zone and then regenerated.

As used throughout the present disclosure, the terms "butenes" or "mixed butenes" are used interchangeably and refer to combinations of one or a plurality of isobutene, 1-butene, trans-2-butene, or cis-2-butene. As used throughout the present disclosure, the term "normal butenes" refers to a combination of one or a plurality of 1-butene, trans-2-butene, or cis-2-butene. As used throughout the present disclosure, the term "2-butenes" refers to trans-2-butene, cis-2-butene, or a combinations of these.

As used throughout the present disclosure, the term "C4" refers to compositions or streams comprising compounds having 4 carbon atoms.

As used in the present disclosure, the term "directly" refers to the passing of materials, such as an effluent, from a first component of a processing system to a second component of the processing system without passing the materials through any intervening components or unit operations that operate to change the chemical identify of one or more constituents or preferentially remove one or more constituents of the effluent. Similarly, the term "directly" also refers to the introducing of materials, such as a feed, to a component of the process system without passing the materials through any preliminary components operable to change the chemical identify of one or more constituents or preferentially remove one or more constituents of the effluent. Intervening or preliminary components or systems operable to change the chemical identify of one or more constituents or preferentially remove one or more constituents of the effluent include reactors and separators, but are not generally intended to include heat exchangers, valves, pumps, sensors, or other ancillary components required for operation of a chemical process.

As used in the present disclosure, the terms "downstream" and "upstream" refer to the positioning of components or unit operations of the processing system relative to a direction of flow of materials through the processing system. For example, a second component is considered "downstream" of a first component if materials flowing through the processing system encounter the first component before encountering the second component. Likewise, the first component is considered "upstream" of the second component if the materials flowing through the processing system encounter the first component before encountering the second component.

As used in the present disclosure, the term "effluent" refers to a stream that is passed out of a reactor, a reaction zone, or a separator following a particular reaction or separation. Generally, an effluent has a different composition than the stream that entered the reactor, reaction zone, or separator. It should be understood that when an effluent is passed to another component or system, only a portion of that effluent may be passed. For example, a slipstream may carry some of the effluent away, meaning that only a portion of the effluent may enter the downstream component or system. The terms "reaction effluent" and "reactor effluent" particularly refer to a stream that is passed out of a reactor or reaction zone.

The term "residence time" refers to the amount of time that reactants are in contact with each other, with a catalyst, or both at reaction conditions, such as at the reaction temperature.

As used in the present disclosure, the term "reactor" refers to any vessel, container, conduit, or the like, in which one or more chemical reactions, such as but not limited catalytic cracking reactions, may occur between one or more reactants optionally in the presence of one or more catalysts. One or more "reaction zones" may be disposed within a reactor. The term "reaction zone" refers to a volume where a particular chemical reaction takes place in a reactor.

As used in the present disclosure, the terms "separation unit" and "separator" refer to any separation device or combinations of separation devices that at least partially separates one or more chemical constituents in a mixture from one another. For example, a separation system selectively separates different chemical constituents from one another, forming one or more chemical fractions. Examples of separation systems include, without limitation, distillation columns, fractionators, flash drums, knock-out drums, knock-out pots, centrifuges, filtration devices, traps, scrubbers, expansion devices, membranes, solvent extraction devices, high-pressure separators, low-pressure separators, or combinations or these. The separation processes described in the present disclosure may not completely separate all of one chemical constituent from all of another chemical constituent. Instead, the separation processes described in the present disclosure "at least partially" separate different chemical constituents from one another and, even if not explicitly stated, separation can include only partial separation.

It should further be understood that streams may be named for the components of the stream, and the component for which the stream is named may be the major component of the stream (such as the component comprising the greatest fraction of the stream). It should also be understood that components of a stream are disclosed as passing from one system component to another when a stream comprising that component is disclosed as passing from that system component to another. For example, a disclosed "mixed butene stream" passing to a first system component or from a first system component to a second system component should be understood to equivalently disclose "mixed butenes" passing to the first system component or passing from a first system component to a second system component.

As previously discussed, greater value light olefins, such as propylene and ethylene, can be produced through steam cracking or fluidized catalytic cracking. However, these processes can produce a significant amount of lower value streams, one of which is a C4 stream comprising mixed butenes and butane, which have lower value compared to propylene and ethylene. In some cases, these C4 streams can be further catalytically cracked to convert mixed butenes from the C4 streams to additional propylene, ethylene, or both. Medium pore zeolites, such as ZSM-5, have been used to catalytically crack mixed butenes to propylene or ethylene. However, the yield of propylene, ethylene, or both from catalytically cracking butenes with zeolites has been limited. Therefore, an ongoing need exists for cracking catalysts and catalytic cracking processes that provide increased conversion of butenes to propylene, ethylene, or both to increase the yield of propylene, ethylene, or both.

The present disclosure is directed to methods of preparing cracking catalysts and processes for catalytic cracking of mixed butenes to produce greater yields of propylene, ethylene, or combinations thereof. The methods of the present disclosure for preparing a cracking catalyst include combining a zeolite, an alumina binder, and phosphoric acid to form an extrusion mixture. The phosphoric acid acts as a peptizing agent. The extrusion mixture comprises from 0.000271 weight percent to 0.1 weight percent phosphoric acid based on the total weight of the extrusion mixture. The methods of the present disclosure for preparing a cracking catalyst further include extruding the extrusion mixture to produce an extrudate. During the extruding, the phosphoric acid peptizes the alumnia binder in the extrudate. The methods of the present disclosure for preparing a cracking catalyst further include drying and calcining the extrudate to produce the cracking catalyst.

As previously discussed, the cracking catalyst includes zeolite. The zeolite may comprise a shape selective zeolite. Shape selective zeolites can be active to catalytically crack hydrocarbon compounds, such as mixed butenes or other olefins, to produce one or more lighter olefins, such as ethylene, propylene, or both. Without being bound by any particular theory, it is believed that the shape selective zeolite may have a greater propensity to crack the relatively lighter hydrocarbons, such as mixed butenes and other olefins, compared to other types of zeolites, such as large pore zeolites. The shape selective zeolite can be an MFI structured zeolite. In embodiments, the shape selective zeolite is ZSM-5 zeolite. As used in the present disclosure, "ZSM-5" refers to zeolites having an MFI framework type according to the IUPAC zeolite nomenclature and consisting of silica and alumina. ZSM-5 refers to "Zeolite Socony Mobil-5" and is a pentasil family zeolite that can be represented by the chemical formula $Na_nAl_aSi_{96-n}O_{192} \cdot 16H_2O$, where $0 < n < 27$.

The ZSM-5 zeolite may have a high molar ratio of silica ($SiO_2$) to alumina ($Al_2O_3$). The ZSM-5 zeolite may have a molar ratio of silica to alumina that is greater than or equal to 500, greater than or equal to 800, greater than or equal to 1000, or even greater than or equal to 1100. The greater molar ratio of silica to alumina may reduce the intensity of the cracking reactions, which may result in reduced formation of side products from the cracking reactions. When the silica to alumina ratio is less than about 500, the acidity of the cracking catalyst may be too great, resulting in increased cracking intensity and formation of side products, resulting in decreased yield of propylene, ethylene, or both. In embodiments, the ZSM-5 zeolite may have a molar ratio of silica to alumina of from 500 to 2000, such as from 500 to 1500, from 500 to 1200, from 800 to 2000, from 800 to 1500, from 800 to 1200, from 1000 to 2000, from 1000, to 1500, from 1000 to 1200, from 1100 to 2000, from 1100 to 1500, from 1100 to 1200, or about 1152.

In embodiments, the ZSM-5 zeolite may have an average surface area of from 200 square meters per gram ($m^2/g$) to 800 $m^2/g$, as determined through the Brunauer-Emmett-Teller (BET) method (average BET surface area). In embodiments, the average BET surface area may be from 200 $m^2/g$ to 400 $m^2/g$, from 200 $m^2/g$ to 600 $m^2/g$, from 200 $m^2/g$ to 800 $m^2/g$, from 300 $m^2/g$ to 400 $m^2/g$, from 300 $m^2/g$ to 600 $m^2/g$, from 300 $m^2/g$ to 800 $m^2/g$, from 400 $m^2/g$ to 600 $m^2/g$, or from 400 $m^2/g$ to 800 $m^2/g$. In embodiments, the ZSM-5 zeolite, can have an average total pore volume per unit weight of the ZSM-5 zeolite of from 0.010 milliliters per gram (mL/g) to 0.500 mL/g, such as from 0.050 mL/g to 0.500 mL/g, from 0.010 mL/g to 0.300 mL/g, or from 0.050 mL/g to 0.300 mL/g.

In embodiments, the cracking catalyst can include from 50 wt. % to 80 wt. % of the ZSM-5 zeolite based on the total weight of the cracking catalyst. In embodiments, the cracking catalyst can include from 50 wt. % to 75 wt. %, from 50 wt. % to 70 wt. %, from 50 wt. % to 69.9 wt. %, 50 wt. % to 65 wt. %, from 50 wt. % to 60 wt. %, from 60 wt. % to 80 wt. %, from 60 wt. % to 75 wt. %, 60 wt. % to 70 wt. %, from 60 wt. % to 69.9 wt. %, from 60 wt. % to 65 wt. %, from 65 wt. % to 80 wt. %, from 65 wt. % to 75 wt. %, from 65 wt. % to 70 wt. %, from 65 wt. % to 69.9 wt. %, from 70 wt. % to 80 wt. %, from 70 wt. % to 75 wt. %, or from 75 wt. % to 80 wt. % of the ZSM-5 zeolite based on the total weight of the cracking catalyst.

As previously discussed, the cracking catalyst may comprise a binder, a matrix material, or both. A refractory binder, matrix material, or both can be utilized to facilitate fabrication of the zeolite particles, to provide strength to the cracking catalyst, and to reduce fabrication costs. Suitable binders include inorganic oxides, such as one or more of alumina, magnesia, zirconia, chromia, titania, boric, phosphate, zinc oxide, silica, or combinations of these. In embodiments, the binder may be an alumina-based binder. One commercial embodiment of an alumina binder is Cataloid AP-3, obtained from Catalysts & Chemicals Industries Co., Ltd (CCIC), Japan. Other alumina binders can also be used. In embodiments, the cracking catalyst can include from greater than or equal to 19 wt. %, greater than or equal to 20 wt. %, greater than or equal to 29 wt. %, or greater than or equal to 30 wt. % alumina binder based on the total weight of the cracking catalyst. The cracking catalyst can include less than or equal to 50 wt. %, less than or equal to 49 wt. %, less than or equal to 45 wt. %, less than or equal to 40 wt. %, less than or equal to 39 wt. %, less than or equal to 35 wt. %, or less than or equal to 30 wt. % alumina binder based on the total weight of the cracking catalyst. In embodiments, the cracking catalyst can include 19 wt. % to 50 wt. %, from 20 wt. % to 50 wt. %, from 20 wt. % to 45 wt. %, from 20 wt. % to 40 wt. %, from 20 wt. % to 35 wt. %, from 20 wt. % to 30 wt. %, from 25 wt. % to 50 wt. %, from 25 wt. % to 45 wt. %, from 25 wt. % to 40 wt. %, from 25 wt. % to 35 wt. %, from 25 wt. % to 30 wt. %, from 30 wt. % to 50 wt. %, from 30 wt. % to 45 wt. %, from 30 wt. % to 40 wt. %, or from 30 wt. % to 35 wt. % alumina binder based on the total weight of the cracking catalyst.

The ratio by weight of zeolite to alumina binder in the cracking catalyst can be from 4 to 1 (about 80 wt. % zeolite and about 20 wt. % alumina binder), from 3 to 1 (about 75 wt. % zeolite and about 25 wt. % alumina binder), or from 2 to 1 (about 66 wt. % zeolite and 33 wt. % alumina binder). In embodiments, the cracking catalyst may comprise 70 wt. % zeolite, from 0.000271 wt. % to 0.1 wt. % phosphoric acid, and the balance the alumina binder based on the total weight of the cracking catalyst. In embodiments, the cracking catalyst can include a ratio by weight of the zeolite to the alumina binder from 3:1 to 2:1. In embodiments, the cracking catalyst can include a ratio by weight of the zeolite to the alumni binder from 3:1 to 2:1, from 8:3 to 2:1, from 3:1 to 5:3, from 4:1 to 1:1, or about 7:3.

The cracking catalyst can be prepared by combining a zeolite, an alumina binder, and phosphoric acid to form an extrusion mixture, extruding the extrusion mixture to produce an extrudate, and drying and calcining the extrudate. In embodiments, after the combining to form an extrusion mixture, the method may further comprise mixing the extrusion mixture for a mixing time of from 1 minute to 30 minutes to produce a consistency of a thick paste. In embodiments, the method may further comprise drying the extrudate for a drying period of from 1 hour to 24 hours. In embodiments, the method may comprise calcining the extrudate under air at a calcining temperature of from 450° C. to 600° C. with a temperature ramping rate of from 0.1° C. per minute to 2° C. per minute for from 2 hours to 8 hours to produce the cracking catalyst.

As previously discussed, the cracking catalyst may be prepared by combining the zeolite, the alumina binder, and the phosphoric acid to form the extrusion mixture. In embodiments, the phosphoric acid is in a solution. In embodiments, the phosphoric acid solution may have a pH from 1 to 5, such as from 1.5 to 4.5, from 2 to 4, from 2.5 to 3.5, or about 3. In embodiments, the phosphoric acid may be added dropwise to the zeolite and alumina binder. In embodiments, the method of preparing the cracking catalyst may comprise combining the zeolite and the alumina binder to form a zeolite mixture and then adding the solution comprising phosphoric acid dropwise to the zeolite mixture to form the extrusion mixture.

Following combining, the extrusion mixture can have a small amount of phosphorous. In embodiments, the extrusion mixture can have a phosphorous content from 0.000271 wt. % to 0.1 wt. %, from 0.000271 wt. % to 0.01 wt. %, from 0.000271 wt. % to 0.001 wt. %, or from 0.000271 wt. % to 0.0005 wt. % based on the total weight of the extrusion mixture. In embodiments, the extrusion mixture can have a phosphorous content of less than or equal to 100 parts per million by weight (ppmw) based on the total weight of the extrusion mixture. In embodiments, the extrudate mixture can include from 20 ppmw to 1000 ppmw phosphorous, such as from 20 ppmw to 500 ppmw, from 20 ppmw to 200 ppmw, from 20 ppmw to 100 ppmw, or from 20 ppmw to 50 ppmw phosphorous based on the total weight of the extrusion mixture. The extrusion mixture may then be extruded to form an extrudate.

The extrusion mixture may be extruded using any suitable extrusion process or extruder system available or to be developed in the future, such as but not limited to screw extruders, twin-screw extruders, piston extruders, other types of extruders, or combinations of these extruders. The extrudate may then be dried. The extrudate may be dried using any suitable drying process or drying system available or to be developed in the future, such as but not limited to air drying on a bench, heat drying, squeeze drying, freeze drying, other types of drying, or combinations of these drying processes or drying systems.

After drying, the extrudate can be calcined to produce the cracking catalyst. In embodiments, the extrudate can be calcined under air at a calcination temperature of from 450° C. to 600° C. for a calcination period of from 4 hours to 8 hours.

In embodiments, the cracking catalyst can include zeolite comprising ZSM-5 zeolite having a silica to alumina molar ratio of from 500 to 2000, or from 1100 to 1200, and about 30 wt. % alumina binder based on the total weight of the cracking catalyst. In embodiments, the cracking catalyst may further comprise a phosphorous content from 0.000271 wt. % to 0.1 wt. %, from 0.000271 wt. % to 0.01 wt. %, from 0.000271 wt. % to 0.001 wt. %, or from 0.000271 wt. % to 0.0005 wt. % based on the total weight of the cracking catalyst. In embodiments, the cracking catalyst can have a phosphorous content of less than or equal to 100 parts per million by weight (ppmw) based on the total weight of the cracking catalyst. In embodiments, the cracking catalyst can include from 20 ppmw to 1000 ppmw phosphorous, such as from 20 ppmw to 500 ppmw, from 20 ppmw to 200 ppmw, from 20 ppmw to 100 ppmw, or from 20 ppmw to 50 ppmw phosphorous based on the total weight of the cracking catalyst.

In embodiments, the cracking catalyst may consist of or consist essentially of ZSM-5 zeolite having a silica to alumina molar ratio of from 500 to 2000, an alumina binder, and less than or equal to 1000 ppmw phosphorous based on the total weight of the cracking catalyst.

The cracking catalyst can be in the form of shaped particles, such as generally spherical catalyst particles. In embodiments, the cracking catalyst can have a particle size of from 212 micrometers to 300 micrometers. The size of the catalyst particles refers to the maximum length of a particle from one side to another, measured along the longest distance of the catalyst particle. For instance, a spherically shaped catalyst particle has a size equal to its diameter, or a rectangular prism shaped catalyst particle has a maximum length equal to the hypotenuse stretching from opposite corners. In embodiments, the method for preparing a cracking catalyst may further comprise pressing the cracking catalyst, and sieving the cracking catalyst to form cracking catalyst particles. In embodiments, the cracking catalyst can be sieved to produce cracking catalyst particles having a particle size of from 212 micrometers to 300 micrometers. Thus, the cracking catalyst can include particles that pass through a 300 micrometer screen but do not pass through a 212 micrometer screen. In embodiments, the cracking catalyst can have an average particle size of from 40 micrometers ($\mu$m) to 600 $\mu$m, such as from 40 $\mu$m to 500 $\mu$m, from 40 $\mu$m to 400 $\mu$m, from 40 $\mu$m to 300 $\mu$m, from 100 $\mu$m to 600 $\mu$m, from 100 $\mu$m to 500 $\mu$m, from 100 $\mu$m to 400 $\mu$m, from 100 $\mu$m to 300 $\mu$m, from 200 $\mu$m to 600 $\mu$m, from 200 $\mu$m to 500 $\mu$m, from 200 $\mu$m to 400 $\mu$m, from 200 $\mu$m to 300 $\mu$m, or from 212 $\mu$m to 300 $\mu$m.

In embodiments, the cracking catalyst may comprise a percent crystallinity of from 95% to 100%. In embodiments, the cracking catalyst may comprise a percent crystallinity of from 95% to 100%, such as from 96% to 99%, from 97% to 99%, or 98%.

In embodiments, the cracking catalyst may have an average BET surface area less than the average BET surface area of the zeolite prior to combining with the alumina binder and phosphoric acid. In embodiments, the cracking catalyst may have an average BET surface area from 300 $m^2$/g to 400 $m^2$/g. In embodiments, the cracking catalyst may have an average BET surface area from 300 $m^2$/g to 400 $m^2$/g, from 325 $m^2$/g to 400 $m^2$/g, from 330 $m^2$/g to 400 $m^2$/g, from 335 $m^2$/g to 400 $m^2$/g, from 335 $m^2$/g to 475 $m^2$/g, from 335 $m^2$/g to 450 $m^2$/g, from 335 $m^2$/g to 445 $m^2$/g, or about 340 $m^2$/g.

As previously discussed, the cracking catalyst of the present disclosure can be used in a process for catalytically cracking mixed butenes and other olefins to produce propylene, ethylene, or both. As previously discussed, the process for catalytically cracking olefins to produce propylene, ethylene, or both can include contacting a feed comprising butenes with the cracking catalyst under reaction conditions, where contacting the feed comprising butenes with the cracking catalyst at the reaction conditions may cause at least a portion of the butenes in the feed to undergo catalytic cracking to produce a cracking effluent comprising at least propylene. In embodiments, the process can include a cracking catalyst comprising a ZSM-5 zeolite having a molar ratio of silica to alumina of from 500 to 2000, an alumina binder, and phosphoric acid. In embodiments, the cracking catalyst may comprise a zeolite to alumina binder ratio of from 3:1 to 2:1 by weight, a percent crystallinity of from 95% to 100%, an average BET surface area of from 300 $m^2$/g to 400 $m^2$/g, and from 0.000271 wt. % to 0.1 wt. % phosphorous based on the total weight of the cracking catalyst.

The feed stream can comprise one or more olefins, such as mixed butenes, mixed pentenes, mixed hexenes, or other olefins. The feed stream can comprise at least mixed butenes, such as but not limited to 1-butene, cis-2-butene, trans-2-butene, isobutene, or combinations of these. In embodiments, the feed stream can be a C4 stream, which can include mixed butenes as well as other C4 compounds, such as but not limited to butane, isobutane, 1,3-butadiene, or combinations of these. In embodiments, the feed stream can be a C4 stream recovered from a steam cracking process or a fluidized catalytic cracking process. In embodiments, the feed stream can comprise, consist of, or consist essentially of 1-butene, 2-butenes, isobutane, and n-butane, where the 2-butenes comprise cis-2-butene, trans-2-butene, or both.

In embodiments, the feed stream can comprise 1-butene. In embodiments, the feed stream can comprise from 12.5 wt. % to 50 wt. % 1-butene based on the total mass flow rate of the feed stream. In embodiments, the feed stream can comprise from 12.5 wt. % to 45 wt. %, from 12.5 wt. % to 40 wt. %, from 20 wt. % to 50 wt. %, from 20 wt. % to 45 wt. %, from 20 wt. % to 40 wt. %, from 25 wt. % to 50 wt. %, from 25 wt. % to 45 wt. %, from 25 wt. % to 40 wt. %, from 30 wt. % to 50 wt. %, from 30 wt. % to 45 wt. %, from 30 wt. % to 40 wt. %, or from 40 wt. % to 50 wt. % 1-butene based on the total mass flow rate of the feed stream. In embodiments, the feed stream can comprise 2-butenes, including cis-2-butene, trans-2-butene, or both. In embodiments, the feed stream can comprise from 12.5 wt. % to 30 wt. % 2-butenes based on the total mass flow rate of the feed stream. In embodiments, the feed stream can comprise from 12.5 wt. % to 25 wt. %, from 12.5 wt. % to 20 wt. %, from 12.5 wt. % to 15 wt. %, from 15 wt. % to 30 wt. %, from 15 wt. % to 25 wt. %, from 15 wt. % to 20 wt. %, from 20 wt. % to 30 wt. %, or from 20 wt. % to 25 wt. % 2-butenes based on the total mass flow rate of the feed stream.

In embodiments, the feed stream can comprise isobutane. In embodiments, the feed stream can comprise from 15 wt. % to 30 wt. % isobutane based on the total mass flow rate of the feed stream. In embodiments, the feed stream can comprise from 15 wt. % to 25 wt. %, from 15 wt. % to 20 wt. %, from 15 wt. % to 30 wt. %, from 15 wt. % to 25 wt. %, from 15 wt. % to 20 wt. %, from 20 wt. % to 30 wt. %, or from 20 wt. % to 25 wt. % isobutane based on the total mass flow rate of the feed stream. In embodiments, the feed stream can comprise n-butane. In embodiments, the feed stream can comprise from 5 wt. % to 55 wt. % n-butane based on the total mass flow rate of the feed stream. In embodiments, the feed stream can comprise from 5 wt. % to 50 wt. %, from 5 wt. % to 45 wt. %, from 5 wt. % to 40 wt. %, from 5 wt. % to 30 wt. %, from 5 wt. % to 10 wt. %, from 10 wt. % to 55 wt. %, from 10 wt. % to 50 wt. %, from 10 wt. % to 45 wt. %, from 10 wt. % to 40 wt. %, from 20 wt. % to 55 wt. %, from 20 wt. % to 50 wt. %, from 20 wt. % to 45 wt. %, from 20 wt. % to 40 wt. %, from 30 wt. % to 55 wt. %, from 30 wt. % to 50 wt. %, from 30 wt. % to 45 wt. %, from 30 wt. % to 40 wt. %, or from 40 wt. % to 55 wt. % n-butane based on the total mass flow rate of the feed stream. The feed stream can also include other C4 constituents, such as but not limited to isobutene, 1,3-butadiene, or other C4 compounds. If present, the 1,3-butadiene concentration in the feed stream can be less than or equal to 0.1 wt. % 1,3-butadiene based on the total mass flow rate of the feed stream.

In embodiments, the feed stream to the catalytic cracking process can be an effluent from a metathesis reactor for converting mixed butenes to propylene, ethylene, or both through one or more metathesis reactions. When the feed stream is an effluent from a metathesis reactor, the feed stream can further include greater molecular weight olefins, such as mixed pentenes, mixed hexenes, or other greater molecular weight olefins resulting from metathesis of mixed butenes. The feed stream can also include propylene, ethylene, or both produced from the metathesis reactions. When the feed stream is an effluent from a metathesis reactor, the feed stream can also include other reaction products resulting from the metathesis reactions.

The feed stream generally does not include nitrogen or air. Without intending to be bound by any particular theory, it is believed that the presence of nitrogen, air, or both can cause side reactions in the cracking reactor resulting in reduced yields of propylene, ethylene, or both. In embodiments, the feed stream is substantially free of nitrogen, air, or both, such as having less than 0.1 wt. % or even less than 0.01 wt. % nitrogen, air, or both based on the total mass flow rate of the feed stream.

Referring now to FIG. 1, a reactor system 10 comprising a cracking reactor 100 for converting the feed stream 102 comprising at least mixed butenes to propylene, ethylene, or both is schematically depicted. The feed stream 102 is passed to the cracking reactor 100, which comprises at least a cracking reaction zone 110 comprising the cracking catalyst 112. In embodiments, the cracking reactor 100 can be a fixed bed reactor. Other types of reactors, such as but not limited to moving bed reactors, fluidized bed reactors, and the like can also be used to for the cracking reactor 100. Although shown as a downflow reactor in FIG. 1, the cracking reactor 100 can also be an upflow reactor, a horizontal flow reactor, or have any other suitable flow pattern suitable for contacting the feed stream 102 with the cracking catalyst 112.

In the cracking reactor 100, the feed stream 102 comprising the mixed butenes can be contacted with the cracking catalyst 112 at reaction conditions sufficient to cause catalytic cracking of at least a portion of the mixed butenes or other olefins in the feed stream 102 to produce a cracking effluent 120 comprising propylene, ethylene, or both. Contact of the mixed butenes or other olefins in the feed stream 102 with the cracking catalyst 112 at the reaction conditions can cause at least a portion of the mixed butenes or other olefins to undergo cracking reactions to convert the olefins into propylene, ethylene, or both. The feed stream 102 can be contacted with the cracking catalyst 112 in the cracking reaction zone 110 at a temperature sufficient to cause cracking of the olefins to produce the cracking effluent 120 comprising propylene, ethylene, or both. In embodiments, the process can include contacting the feed stream 102 with the cracking catalyst 112 at a temperature of from 300° C. to 650° C., such as from 300° C. to 600° C., from 300° C. to 550° C., from 300° C. to 500° C., from 350° C. to 650° C., from 350° C. to 600° C., from 350° C. to 550° C., from 350° C. 500° C., from 400° C. to 650° C., from 400° C. to 600° C., from 400° C. to 550° C., from 400° C. to 500° C., from 450° C. to 600° C., from 450° C. to 550° C., or from 500° C. to 600° C. In embodiments, the feed stream 102 can be contacted with the cracking catalyst 112 in the cracking reaction zone 110 at a pressure of from 1 bar (100 kPa) to 30 bar (3,000 kPa) or from 2 bar (200 kPa) to 20 bar (2,000 kPa). In embodiments, the feed stream 102 can be contacted with the cracking catalyst 112 in the cracking reaction zone 110 at atmospheric pressure. In embodiments, the feed stream 102 can be contacted with the cracking catalyst 112 in the cracking reaction zone 110 at a weight hourly space velocity (WHSV) of from 3 per hour ($h^{-1}$) to 10,000 $h^{-1}$, such as from 3 $h^{-1}$ to 5000 $h^{-1}$, from 3 $h^{-1}$ to 2500 $h^{-1}$, from 3 $h^{-1}$ to 1000 $h^{-1}$, from 3 $h^{-1}$ to 100 $h^{-1}$, from 3 $h^{-1}$ to 12 $h^{-1}$, from 100 $h^{-1}$ to 5000 $h^{-1}$, or from 300 $h^{-1}$ to 2500 $h^{-1}$.

The cracking catalyst 112 may be activated by passing a flow of nitrogen gas through the cracking catalyst 112 at elevated temperature prior to contacting the feed stream 102 with the cracking catalyst 112 in the cracking reaction zone 110. In embodiments, the processes of the present disclosure can include, before contacting the feed stream 102 with the cracking catalyst 112, activating the cracking catalyst 112 with a flow of nitrogen gas at a temperature of from 450° C. to 650° C., or about 550° C. for a period of from 8 hours to 24 hours.

Figure 2:
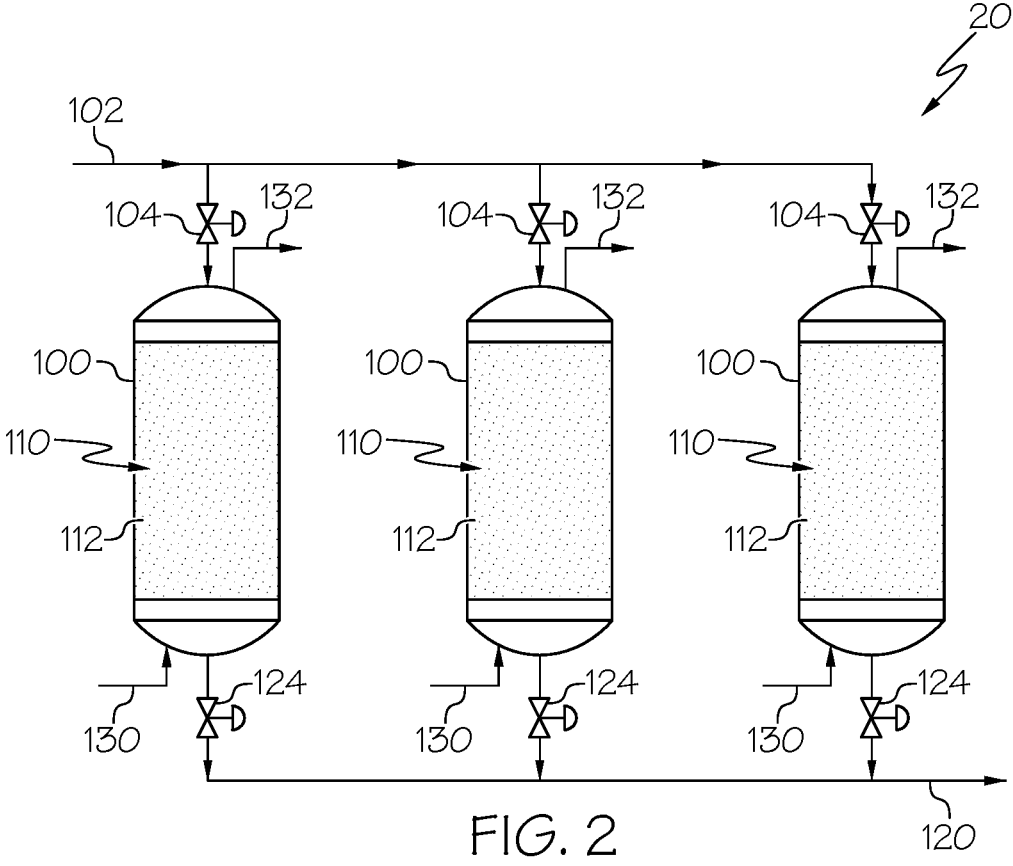
FIG. 2 schematically depicts a generalized flow diagram of a cracking reactor system comprising a plurality of fixed bed reactors for converting mixed butenes to propylene, ethylene, or both through catalytic cracking, according to one or more embodiments shown and described in the present disclosure.

Referring now to FIG. 2, in embodiments, a reactor system 20 for converting mixed butenes and other olefins to propylene and ethylene can include a plurality of reactors 100 that can be operated in parallel. Although shown in FIG. 2 as having three reactors 100, the reactor system 20 having a plurality of reactors 100 can have 2, 3, 4, 5, 6, 7, 8, or more than 8 reactors 100 operated in parallel. Each of the plurality of reactors 100 can include an inlet valve 104 that can be operable to control the flow of the feed stream 102 to each of the plurality of reactors 100. Each of the plurality of reactors 100 can also include an outlet valve 124 that can be operable to control the flow of the cracking effluent 120 from each of the reactors 100. Each cracking reactor 100 can also, optionally, include a regenerating fluid inlet 130 and a regenerating fluid outlet 132, which can be used during regeneration of the cracking catalyst 112. As shown in FIG. 2, the regenerating fluid inlet 130 and regenerating fluid outlet 132 are arranged to produce a flow of regenerating fluid counter to the flow of the reactants through the cracking reaction zone 110. However, it is understood that the regenerating fluid inlet 130 and regenerating fluid outlet 132 could be configured to direct a regenerating fluid in the same direction as the reactants flow through the cracking reaction zone 110.

The reactor system 20 can be operated in a swing mode where the feed stream 102 can be passed to a first subset of the reactors 100 of the system 20 while a second subset of the reactors 100 of the system 20 are subjected to regeneration or reconditioning of the cracking catalyst 112 or replacement of the cracking catalyst 112. The feed stream 102 can be passed to the first subset of reactors 100 until the composition of the cracking effluent 120 indicates that the cracking catalyst 112 in the cracking reaction zone 110 of the first subset of reactors 100 is due for regeneration. Regeneration, reconditioning, or replacement of the cracking catalyst 112 is indicated when the activity of the cracking catalyst 112 has decreased, resulting in an unacceptable decrease in yield of propylene and ethylene in the cracking effluent 120. When the cracking effluent 120 indicates reduced catalytic activity, the feed stream 102 can be diverted to the second subset of reactors 100 by changing the positions of the inlet valves 104 and the outlet valves 124 for the reactors in the first subset and second subset of the reactors 100. Then, the feed stream 102 can be contacted with cracking catalyst 112—which has been regenerated, reconditioned, or replaced—in the second subset of reactors 100 while the used cracking catalyst 112 in the first subset of reactors 100 is being regenerated, reconditioned, or replaced.

Figure 3:
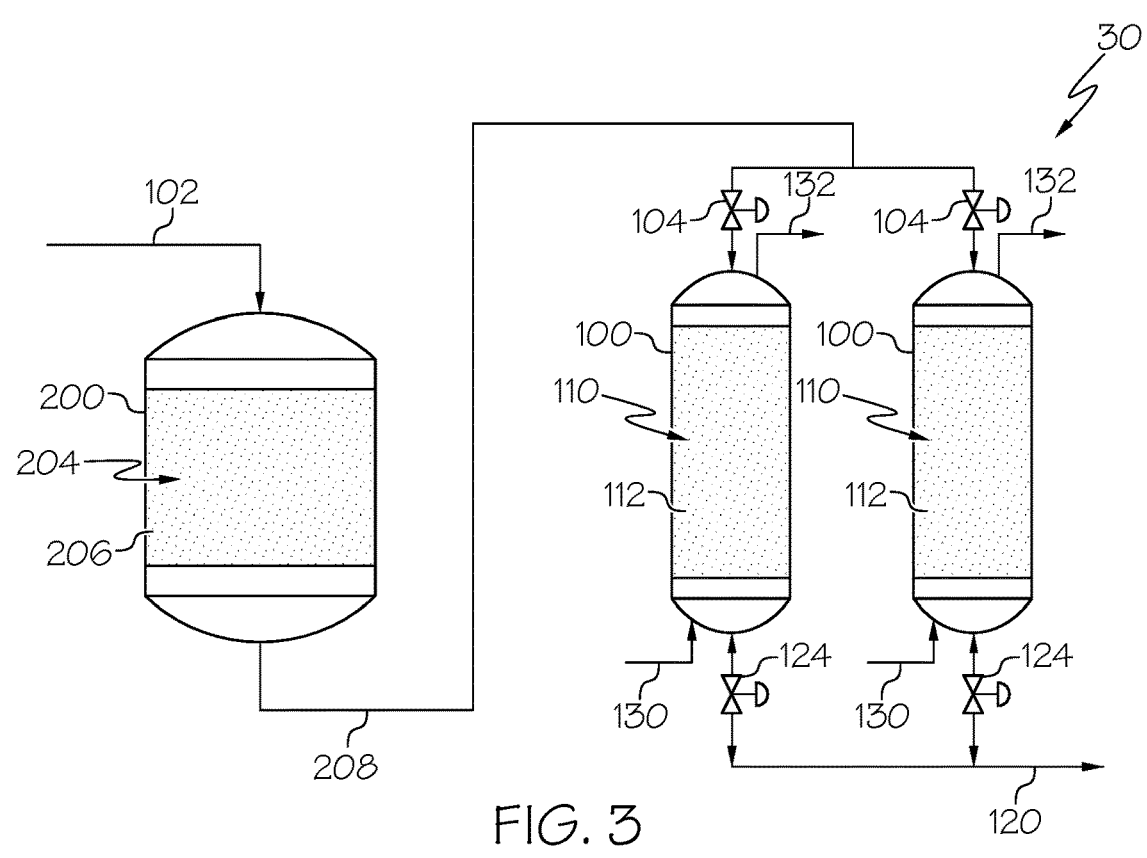
FIG. 3 schematically depicts a generalized flow diagram of a system for converting mixed butenes to propylene, ethylene, or both through metathesis and catalytic cracking, according to one or more embodiments shown and described in the present disclosure.

Referring now to FIG. 3, in embodiments, the cracking catalyst can be used in a dual metathesis and cracking system 30 for converting mixed butenes to propylene, ethylene, or both through a combination of metathesis and cracking. The dual metathesis and cracking system 30 can include a metathesis reactor 200 comprising a metathesis reaction zone 204 that includes a metathesis catalyst 206, such as but not limited to a tungsten or tungsten oxide catalyst supported on a silica, alumina, or a silica-alumina support. The dual metathesis and cracking system 30 can further include at least one cracking reactor 100 disposed downstream of the metathesis reactor 200. In the dual metathesis and cracking system 30 of FIG. 3, the feed stream 102 is passed to the metathesis reactor 200, where the feed stream 102 is contacted with the metathesis catalyst 206 in the metathesis reaction zone 204 at metathesis reaction conditions. Contact of the feed stream 102 with the metathesis catalyst 206 at metathesis reaction conditions can cause at least a portion of the mixed butenes to undergo metathesis reactions to produce other olefins, such as but not limited to propylene, ethylene, pentene, hexene, or combinations of these. The metathesis reaction conditions can be similar to the cracking reaction conditions previously discussed. In embodiments, the feed stream 102 can be contacted with the metathesis catalyst 206 at a temperature of from 300° C. to 650° C., a pressure of from 1 bar (100 kPa) to 30 bar (3,000 kPa), and a weight hourly space velocity (WHSV) of from 3 per hour ($h^{-1}$) to 10,000 $h^{-1}$. The metathesis effluent 208 can be passed out of the metathesis reactor 200. The metathesis effluent 208 can include propylene, ethylene, unreacted mixed butenes, mixed pentenes, mixed hexenes, butane, isobutane, or combinations of these.

The metathesis effluent 208 can be passed from the metathesis reactor 200 to the cracking reactor 100, where the metathesis effluent 208 is contacted with the cracking catalyst 112 in the cracking reaction zone 110. In embodiments, the metathesis effluent 208 can be passed directly from the metathesis reactor 200 to the cracking reactor 100 without separation or any other intervening unit operation. The cracking reaction conditions can be any of the reaction conditions previously discussed for the cracking reactor 100. Contacting the metathesis effluent 208 with the cracking catalyst 112 in the cracking reaction zone 110 can cause cracking reactions that can convert, mixed pentenes, mixed hexenes, unreacted mixed butenes or combinations of these to produce additional propylene, ethylene, or both. Thus, the cracking effluent 120 passed out of the cracking reactors 100 can have a greater concentration and yield of propylene, ethylene, or both compared to the metathesis effluent 208. In embodiments, the process may yield at least 25% olefins by weight of the total product yield. In embodiments, the process may yield at least 25% olefins, at least 30% olefins, at least 31% olefins, at least 32% olefins, or at least 33% olefins by weight of the total product yield.

Figure 4:
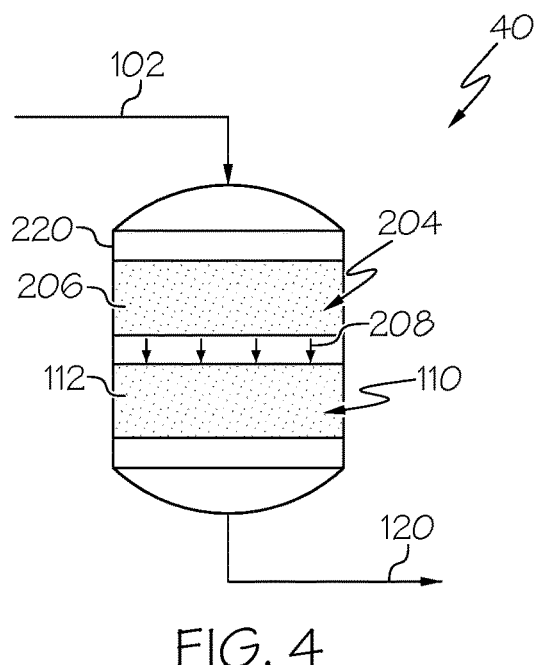
FIG. 4 schematically depicts a generalized flow diagram of a another system for converting mixed butenes to propylene, ethylene, or both through metathesis and catalytic cracking, according to one or more embodiments shown and described in the present disclosure.

Referring now to FIG. 4, in embodiments, the cracking catalyst 112 of the present disclosure can be incorporated into a dual metathesis and cracking system 40 that comprises a combined metathesis and cracking reactor 220 that includes a metathesis reaction zone 204 and a cracking reaction zone 110 disposed in the same metathesis and cracking reactor 220. The cracking reaction zone 110 comprising the cracking catalyst 112 can be disposed downstream of the metathesis reaction zone 204 comprising the metathesis catalyst 206. The metathesis effluent 208 can pass directly from the metathesis reaction zone 204 to the cracking reaction zone 110. The combined metathesis and cracking reactor 220 can be operated at any of the operating conditions previously discussed.

Figure 5:
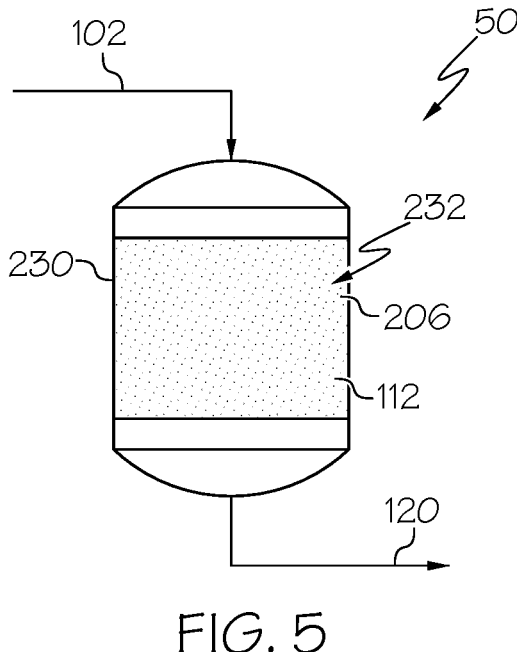
FIG. 5 schematically depicts a generalized flow diagram of still another system for converting mixed butenes to propylene, ethylene, or both through metathesis and catalytic cracking, according to one or more embodiments shown and described in the present disclosure.

Referring now to FIG. 5, in some embodiments, the cracking catalyst 112 of the present disclosure can be incorporated into a metathesis and cracking system 50 in which the cracking catalyst 112 is combined and mixed with the metathesis catalyst 206 in a combined reaction zone 232 in a combined metathesis and cracking reactor 230.

EXAMPLES

The various embodiments of cracking catalysts and processes will be further clarified by the following examples. The examples are illustrative in nature, and should not be understood to limit the subject matter of the present disclosure.

Example 1: Preparation of Cracking Catalyst

In Example 1, a cracking catalyst comprising ZSM-5 was prepared according to the methods of the present disclosure. In particular, a ZSM-5 zeolite was scaled up using an alumina binder and phosphoric acid. First, 1.2 grams (g) of a Cataloid AP-3™ brand alumina based binder available from Catalysts & Chemicals Industries Co., Ltd (CCIC), Japan), and 2.8 g of ZSM-5 with a $SiO_2$-to-$Al_2O_3$ molar ratio (SAR) of 1152, commercially available as ZD05020 from ZEOLYST International were physically mixed in a nonstick beaker for 10 minutes (min). Second, three milliliters (mL) of phosphoric acid solution with a pH of 3 was then added dropwise to the beaker with mixing until a thick paste was formed. The thick paste was then extruded and left to dry for 3 hours. The extrudate was then calcined under air at 500° C., with a temperature ramping rate of 0.5° C. per minute for 4 hours to produce the cracking catalyst of Example 1.

Comparative Example 2: Comparative Cracking Catalyst

The ZSM-5 with a $SiO_2$-to-$Al_2O_3$ molar ratio (SAR) of 1152, commercially available as ZD05020 from ZEOLYST International was used as a comparative catalyst.

Example 3: Characterization of Cracking Catalyst of Example 1

In Example 3, the cracking catalyst of Example 1 and the ZSM-5 zeolite of Comparative Example 2 were evaluated for crystallinity, and BET surface area. The crystallographic structures of the cracking catalyst of Example 1 and the ZSM-5 zeolite of Comparative Example 2 were determined through X-Ray Diffraction (XRD) using a Model D4 ENDEAVOR™ x-ray diffractometer commercially available from Burker, using CuKα radiation and a Ni filter, in the 0-90 degree range. Table 1 shows the crystallinity percentage of both the scaled up cracking catalyst of Example 1 and the ZSM-5 zeolite of Comparative Example 2. As shown below in Table 1, extruding the ZSM-5 with the binder and the phosphoric acid peptizer did not significantly affect the crystallinity of the cracking catalyst of Example 1 compared to the crystallinity of the ZSM-5 of Comparative Example 2.

TABLE 1

| XRD Crystallinity Percentage of Example 1 and Comparative Example 2 | |
| --- | --- |
| Catalyst | Crystallinity % |
| Comparative Example 2 | 100 |
| Example 1 | 98 |

The average BET surface area of the catalysts of Example 1 and Comparative Example 2 described above were measured with $N_2$ physisorption using an AUTOROB™ iQ-C instrument commercially available from Quantachrom. Table 2 shows the average BET surface area of the catalysts of Example 1 and Comparative Example 2. The catalyst of Example 1 had a significantly lower average BET surface area compared to the ZSM-5 zeolite of Comparative Example 2, showing that the extrusion of ZSM-5 using phosphoric acid results in a reduction of average BET surface area.

TABLE 2

| Average BET Surface Area of Example 1 and Comparative Example 2 | |
| --- | --- |
| Catalyst | Average BET Surface Area (m²/g) |
| Comparative Example 2 | 414.0 |
| Example 1 | 340.5 |

Example 4: Catalytic Cracking Performance

In Example 4, the performance of the cracking catalyst of Example 1 was evaluated in comparison to the ZSM-5 zeolite of Comparative Example 2. The catalytic performance tests were carried out using high-throughput screening reactors commercially available from the HTE Company. All catalysts were pressed and sieved to 212 μm to 300 μm before testing.

Figure 6:
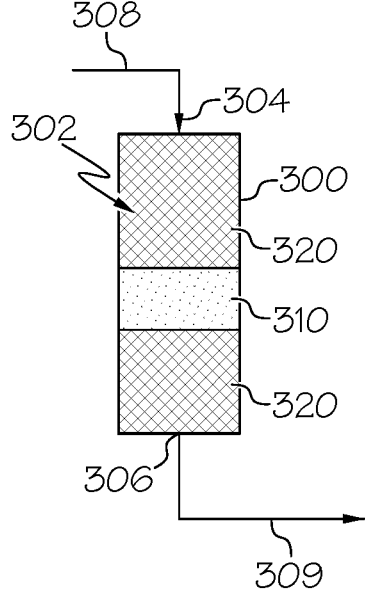
FIG. 6 schematically depicts one reactor compartment of a screening reactor system for evaluating the catalysts of the examples, according to one or more embodiments shown and described in the present disclosure.

Referring now to FIG. 6, one reactor 300 of the high-throughput screening reactors for evaluating the cracking catalyst is schematically depicted. Each reactor 300 includes a reaction chamber 302 having an inlet 304 and an outlet 306. The cracking catalyst 310 is placed in the reaction chamber 302 between two layers of silicon carbide 320. A Weight Hourly Space Velocity (WHSV) of 5 with respect to the cracking catalyst of Example 1 and the ZSM-5 zeolite of Comparative Example 2, respectively, was used for the catalytic performance test. For the cracking catalyst of Example 1, 0.1 g of cracking catalyst (which comprised 0.07 g ZSM-5 zeolite) was used. For the catalyst of Comparative Example 2, 0.07 g of ZSM-5 zeolite was used. Thus, an equal mass of the ZSM-5 zeolite was used for each of Example 1 and Comparative Example 2. The reactor temperature was monitored by thermocouple 330 placed at three difference locations to ensure isothermal heating across the reactors 300.

The reactors were heated to 120° C. under nitrogen and argon (total flow rate: Ar=6 mL/min, and $N_2$=120 mL/min) to ensure slow moisture desorption from catalysts and no gas leakage by monitoring inlet and outlet argon mass flowrate for 24 hours. Reactor temperature was monitored by thermocouples placed at three different locations to ensure isothermal heating across the reactors. The catalysts were then activated under nitrogen with a total flowrate of 120 mL per min at 550° C. for 24 hours. Then, the reactors were cooled down to 500° C. under nitrogen. At 500° C., nitrogen was turned off and a mixed butene feed with the composition shown in Table 3 was fed for 90 hours. The mixed butane feed was fed at a flow rate of 0.267 g per min across 16 reactors.

TABLE 3

| Mixed Butene Feed Composition in Weight Percent | |
| --- | --- |
| Component | Weight Percent |
| 1-Butene | 45 |
| Cis-2-butene | 12.5 |
| Trans-2-butene | 12.5 |
| Iso-butane | 20 |
| n-butane | 10 |

Figure 7:
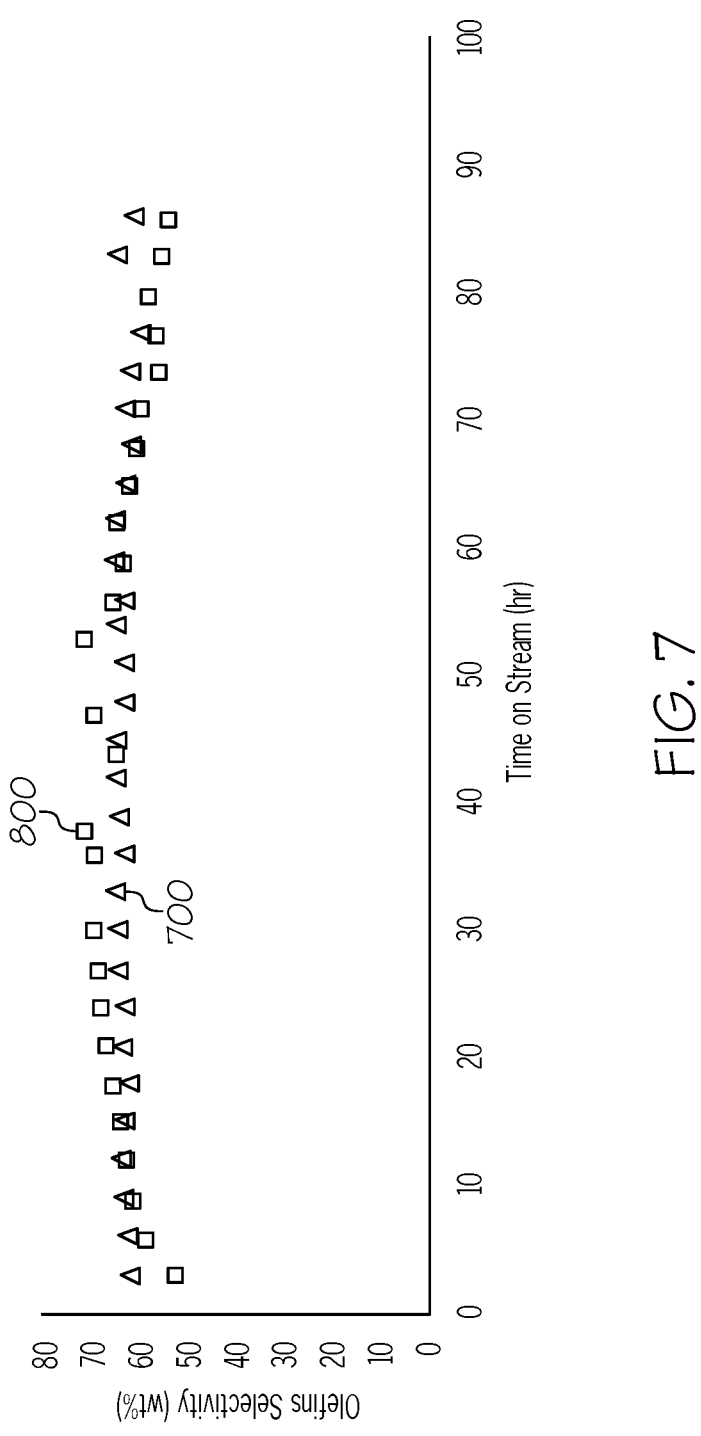
FIG. 7 graphically depicts olefin selectivity by percent weight (y-axis) with respect to time (x-axis) for cracking a mixed butene feed using the cracking catalyst of Example 1 compared to the cracking catalyst of Comparative Example 2, according to one or more embodiments shown and described in the present disclosure.

An online gas chromatographer, commercially available as model 7890B from Agilent, using helium as a carrier gas, was used to analyze the products. The gas chromatographer used a thermal conductivity detector (TDC) to identify light gases and used two flame ionization detectors (FID) detectors to identify $C_1$-$C_6$ hydrocarbons. FIG. 7 depicts the catalytic performance of the catalysts of Example 1 700 and Comparative Example 2 800 as a function of time. Table 4 shows the olefin yield (i.e. the combined ethylene and propylene yield) for the catalysts of Example 1 and Comparative Example 2, as well as their respective selectivity for yielding olefins. As shown in Table 4, the catalyst of Example 1 produced a higher olefin yield and had a higher selectivity, thus showing that using a phosphoric acid peptizer significantly increases olefin yield and selectivity.

TABLE 4

| Average Catalytic Performance with Mixed Butene Feed | | | | |
| --- | --- | --- | --- | --- |
| Temperature (° C.) | Catalyst | Olefins Yield (Weight Percent) | Olefins Selectivity | Percent Improvement (Olefins Yield) |
| 500 | Comparative Example 2 | 32.23 | 0.601 | 3.7 |
| | Example 1 | 33.43 | 0.626 | |

According to a first aspect of the present disclosure, a method for preparing a cracking catalyst includes combining a zeolite, an alumina binder, and phosphoric acid to form an extrusion mixture. The phosphoric acid acts as a peptizing agent. The extrusion mixture comprises from 0.000271 weight percent to 0.1 weight percent phosphoric acid based on the total weight of the extrusion mixture. The method may further include extruding the extrusion mixture to produce an extrudate. During the extruding, the phosphoric acid peptizes the alumina binder in the extrudate. The method may further include drying and calcining the extrudate to produce the cracking catalyst.

A second aspect of the present disclosure may include the first aspect, and may further include pressing the cracking catalyst, and sieving the cracking catalyst to form cracking catalyst particles.

A third aspect of the present disclosure may include either one of the first or second aspects, where a ratio by weight of the zeolite to the alumina binder is from 3:1 to 2:1.

A fourth aspect of the present disclosure may include any of the first through third aspects, where the phosphoric acid is in a solution and the pH of the solution is from 1 to 5.

A fifth aspect of the present disclosure may include any of the first through fourth aspects, further including adding the phosphoric acid dropwise to the zeolite and the alumina binder.

A sixth aspect of the present disclosure may include any of the first through fifth aspects, including combining the zeolite and the alumina binder to form a zeolite mixture and then adding a solution comprising the phosphoric acid dropwise to the zeolite mixture to form the extrusion mixture.

A seventh aspect of the present disclosure may include any of the first through sixth aspects, where the cracking catalyst comprises from 0.000271 weight percent to 0.1 weight percent phosphorous compounds based on the total weight of the cracking catalyst.

An eighth aspect of the present disclosure may include any of the first through seventh aspects, where the zeolite comprises ZSM-5.

A ninth aspect of the present disclosure may include any of the first through eighth aspects, where the zeolite has a molar ratio of silica to alumina of from 500 to 2000.

A tenth aspect of the present disclosure includes any of the first through ninth aspects, including, after the combining, mixing the extrusion mixture for a mixing time of from 1 minute to 30 minutes to produce a consistency of a thick paste, drying the extrudate for a drying period of from 1 hour to 24 hours, and calcining the extrudate under air at a calcining temperature of from 450° C. to 600° C. with a temperature ramping rate of from 0.1° C. per minute to 2° C. per minute for from 2 hours to 8 hours to produce the cracking catalyst.

An eleventh aspect of the present disclosure includes a cracking catalyst prepared by the method of any of the first through tenth aspects.

A twelfth aspect of the present disclosure includes the cracking catalyst of the eleventh aspect, where the cracking catalyst comprises a percent crystallinity of from 95% to 100%.

A thirteenth aspect of the present disclosure includes the cracking catalyst of the eleventh or twelfth aspects, where the cracking catalyst comprises a Brunauer-Emmett-Teller (BET) surface area of from 300 square meters per gram (m²/g) to 400 m²/g.

A fourteenth aspect of the present disclosure includes the cracking catalyst of any of the eleventh through thirteenth aspects, where the cracking catalyst comprises a pore volume of from 200 m²/g to 800 m²/g, as determined through the Brunauer-Emmett-Teller (BET) method.

A fifteenth aspect of the present disclosure includes the cracking catalyst of any of the eleventh through fourteenth aspects, where the cracking catalyst comprises from 20 parts per million by weight (ppmw) to 100 ppmw phosphorous.

A sixteenth aspect of the present disclosure includes the cracking catalyst of any of the eleventh through fifteenth aspects, where the cracking catalyst comprises particles having an average particle size of from 212 μm to 300 μm.

A seventeenth aspect of the present disclosure includes a process for cracking butenes, the process including contacting a feed comprising the butenes with the cracking catalyst of any of the eleventh through sixteenth aspects under reaction conditions, where contacting the feed comprising butenes with the cracking catalyst of any of the eleventh through sixteenth aspects at the reaction conditions causes at least a portion of the butenes in the feed to undergo catalytic cracking to produce a cracking effluent including at least propylene.

An eighteenth aspect of the present disclosure includes the process of the seventeenth aspect, including contacting the feed comprising butene with the cracking catalyst at a temperature of from 300° C. to 650° C.

A nineteenth aspect of the present disclosure includes either the seventeenth aspect or the eighteenth aspect, where the process yields at least 25% olefins by weight of the total product yield.

A twentieth aspect includes a process for cracking butenes, the process including contacting a feed comprising the butenes with a cracking catalyst under reaction conditions, where contacting the feed comprising butenes with the cracking catalyst causes at least a portion of the butenes in the feed to undergo catalytic cracking to produce a cracking effluent comprising at least propylene, and the cracking catalyst includes a ZSM-5 zeolite having a molar ratio of silica to alumina of from 500 to 2000, an alumina binder, and phosphoric acid, where a zeolite to alumina binder ratio of from 3:1 to 2:1 by weight, a percent crystallinity of from 95% to 100%, a Bruauer-Emmett-Teller (BET) surface area of from 300 square meters per gram (m²/g) to 400 m²/g, and from 0.000271 weight percent to 0.1 weight percent phosphorous based on the total weight of the cracking catalyst.

It is noted that any two quantitative values assigned to a property may constitute a range of that property, and all combinations of ranges formed from all stated quantitative values of a given property are contemplated in this disclosure.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific aspects, it is noted that the various details of such aspects should not be taken to imply that these details are essential components of the aspects. Rather, the claims appended hereto should be taken as the sole representation of the breadth of the present disclosure and the corresponding scope of the various aspects described in this disclosure. Further, it will be apparent that modifications and variations are possible without departing from the scope of the appended claims.

What is claimed is:

1. A method for preparing a cracking catalyst, the method comprising:
   combining a zeolite, an alumina binder, and phosphoric acid to form an extrusion mixture, where:
   the phosphoric acid acts as a peptizing agent; and
   the extrusion mixture comprises from 0.000271 weight percent to 0.1 weight percent phosphoric acid based on the total weight of the extrusion mixture;
   extruding the extrusion mixture to produce an extrudate, where during the extruding, the phosphoric acid peptizes the alumina binder in the extrudate; and
   drying and calcining the extrudate to produce the cracking catalyst.

2. The method of claim 1, further comprising:
   pressing the cracking catalyst; and
   sieving the cracking catalyst to form cracking catalyst particles.

3. The method of claim 1, where a ratio by weight of the zeolite to the alumina binder is from 3:1 to 2:1.

4. The method of claim 1, where the phosphoric acid is in a solution and the pH of the solution is from 1 to 5.

5. The method of claim 1, comprising adding the phosphoric acid dropwise to the zeolite and the alumina binder.

6. The method of claim 1, comprising combining the zeolite and the alumina binder to form a zeolite mixture and then adding a solution comprising the phosphoric acid dropwise to the zeolite mixture to form the extrusion mixture.

7. The method of claim 1, where the cracking catalyst comprises from 0.000271 weight percent to 0.1 weight percent phosphorous compounds based on the total weight of the cracking catalyst.

8. The method of claim 1, where the zeolite comprises ZSM-5.

9. The method of claim 1, where the zeolite has a molar ratio of silica to alumina of from 500 to 2000.

10. The method of claim 1, comprising:

after the combining, mixing the extrusion mixture for a mixing time of from 1 minute to 30 minutes to produce a consistency of a paste;

drying the extrudate for a drying period of from 1 hour to 24 hours; and calcining the extrudate under air at a calcining temperature of from 450° C. to 600° C. with a temperature ramping rate of from 0.1° C. per minute to 2° C. per minute for from 2 hours to 8 hours to produce the cracking catalyst.

11. A cracking catalyst prepared by the method of claim 1.

12. The cracking catalyst of claim 11, where the cracking catalyst comprises a percent crystallinity of from 95% to 100%.

13. The cracking catalyst of claim 11, where the cracking catalyst comprises a Brunauer-Emmett-Teller (BET) surface area of from 300 square meters per gram ($m^2$/g) to 400 $m^2$/g.

14. The method of claim 11, where the cracking catalyst comprises from 20 parts per million by weight (ppmw) to 100 ppmw phosphorous.

15. The method of claim 11, where the cracking catalyst comprises particles having an average particle size of from 212 μm to 300 μm.

16. A process for cracking butenes, the process comprising contacting a feed comprising the butenes with the cracking catalyst of claim 11 under reaction conditions, where contacting the feed comprising butenes with the cracking catalyst at the reaction conditions causes at least a portion of the butenes in the feed to undergo catalytic cracking to produce a cracking effluent comprising at least propylene.

17. The process of claim 16, comprising contacting the feed comprising butene with the cracking catalyst at a temperature of from 300° C. to 650° C.

18. The process of claim 16, where the process yields at least 25% olefins by weight of the total product yield.

19. A process for cracking butenes, the process comprising contacting a feed comprising the butenes with a cracking catalyst under reaction conditions, where contacting the feed comprising butenes with the cracking catalyst causes at least a portion of the butenes in the feed to undergo catalytic cracking to produce a cracking effluent comprising at least propylene; and the cracking catalyst comprises:

a ZSM-5 zeolite having a molar ratio of silica to alumina of from 500 to 2000;

an alumina binder; and phosphoric acid, where:

a zeolite to alumina binder ratio of from 3:1 to 2:1 by weight;

a percent crystallinity of from 95% to 100%;

a Bruauer-Emmett-Teller (BET) surface area of from 300 square meters per gram ($m^2$/g) to 400 $m^2$/g; and from 0.000271 weight percent to 0.1 weight percent phosphorous based on the total weight of the cracking catalyst.

* * * * *